United States Patent
Quelever et al.

(10) Patent No.: US 9,709,615 B2
(45) Date of Patent: Jul. 18, 2017

(54) COMPOSITION SIMULATING THE DIELECTRIC PROPERTIES OF THE HUMAN BODY AND USE THEREOF FOR SAR MEASUREMENT

(71) Applicant: ART-FI, Orsay (FR)

(72) Inventors: Kristell Quelever, Orsay (FR);
Thibaud Coradin, Paris (FR);
Christian Bonhomme, Paris (FR);
Olivier Meyer, Gif-sur-Yvette (FR);
Benoit Derat, Orsay (FR)

(73) Assignee: ART-FI, Orsay (FR)

( * ) Notice: Subject to any disclaimer, the term of this patent is extended or adjusted under 35 U.S.C. 154(b) by 223 days.

(21) Appl. No.: 14/361,104

(22) PCT Filed: Nov. 29, 2012

(86) PCT No.: PCT/EP2012/074007
§ 371 (c)(1),
(2) Date: May 28, 2014

(87) PCT Pub. No.: WO2013/079621
PCT Pub. Date: Jun. 6, 2013

(65) Prior Publication Data
US 2014/0368218 A1    Dec. 18, 2014

(30) Foreign Application Priority Data

Nov. 29, 2011  (EP) .................................... 11306584

(51) Int. Cl.
*G01R 29/08*    (2006.01)
*G09B 23/28*    (2006.01)
(Continued)

(52) U.S. Cl.
CPC ............ *G01R 29/0857* (2013.01); *A61K 8/04* (2013.01); *A61K 8/042* (2013.01); *A61K 8/06* (2013.01);
(Continued)

(58) Field of Classification Search
CPC .. G09B 23/286; G01R 29/0857; B01J 13/003; B01J 13/0052; A61K 8/04; A61K 8/042; A61K 8/06; A61K 8/062
See application file for complete search history.

(56) References Cited

U.S. PATENT DOCUMENTS 4,127,460 A * 11/1978 Gaske ...................... C09D 4/00
522/84
4,848,981 A *  7/1989 Kasprzak ............. C11D 3/3742
427/387
(Continued)

FOREIGN PATENT DOCUMENTS

JP    S63107740    5/1988
JP    H11262653    9/1999
(Continued)

OTHER PUBLICATIONS

Gabriel S. et al., "The dielectric properties of biological tissues: II. Measurements in the frequency range 10 Hz to 20 GHz", Physics in Medicine and Biology, 1996, pp. 2251-2269, vol. 41, IOPScience.
(Continued)

*Primary Examiner* — David Porta
*Assistant Examiner* — Mindy Vu
(74) *Attorney, Agent, or Firm* — Young & Thompson

(57) ABSTRACT

An oil-in-water emulsion includes an aqueous phase and an oily phase, the aqueous phase including water and a relaxing agent, and the oily phase including an oil and at least one surfactant. The emulsion has dielectric properties simulating dielectric properties of the human body. A device including
(Continued)

the emulsion, a simulated human body part filled with the emulsion; and at least one system capable of measuring a local specific absorption rate when the simulated human body part is exposed to an electromagnetic field are also described. A method for conducting specific absorption rate tests of an apparatus radiating an electromagnetic field including using the emulsion, and a process for manufacturing the emulsion are also described.

12 Claims, 8 Drawing Sheets

(51) Int. Cl.
 *B01J 13/00* (2006.01)
 *A61K 8/04* (2006.01)
 *A61K 8/06* (2006.01)
(52) U.S. Cl.
 CPC ............ *A61K 8/062* (2013.01); *B01J 13/003* (2013.01); *B01J 13/0052* (2013.01); *G09B 23/286* (2013.01)

(56) References Cited

U.S. PATENT DOCUMENTS

| 5,376,369 | A | * | 12/1994 | Allison | A61K 9/1075 424/278.1 |
|---|---|---|---|---|---|
| 6,149,926 | A | * | 11/2000 | Venkitaraman | A61K 8/0208 424/401 |
| 2011/0287073 | A1 | | 11/2011 | Strauss | |
| 2013/0099119 | A1 | | 4/2013 | Derat et al. | |

FOREIGN PATENT DOCUMENTS

| JP | 2006078232 | 3/2006 |
|---|---|---|
| JP | 2011080882 | 4/2011 |
| WO | 2011080332 | 7/2011 |
| WO | 2011127163 | 10/2011 |

OTHER PUBLICATIONS

Drossos A. et al., "The dependence of electromagnetic energy absorption upon human head tissue composition in the frequency range of 300-3000 MHz," IEEE Transactions on Microwave Theory and Techniques, 2000, pp. 1988-1995, vol. 48, No. 11.
Fukunaga K. et al., "Dielectric properties of tissue-equivalent liquids and their effects on specific absorption rate" IEEE Transactions on Electromagnetic Compatibility, 2004, pp. 126-129, vol. 46, No. 1.
Okano Y. et al: "The comparison measurement for SAR by thermal evaluation and the electric field probe", Proceedings, 18Th International Zurich Symposium on EMC, 2007, pp. 147-150, Munich.
Kuster N et al: "Energy absorption mechanism by biological bodies in the near field of dipole antennas above 300 MHz", IEEE Transactions on vehicular technology, 1992, pp. 17-23, vol. 41, No. 1, IEEE Service Center, USA.
IEEE Recommended Practice for Determining the Peak Spatial-Average Specific Absorption Rate (SAR) in the Human Head From Wireless Communications Devices: Measurement Techniques, IEEE Std 1528-2003, 2003, pp. 1-149, IEEE, USA.
International Search Report dated Mar. 21, 2013 from corresponding PCT application PCT/EP2012/074007.
Written opinion of the International Searching Authority dated May 29, 2014 from corresponding PCT application PCT/EP2012/074007.

\* cited by examiner

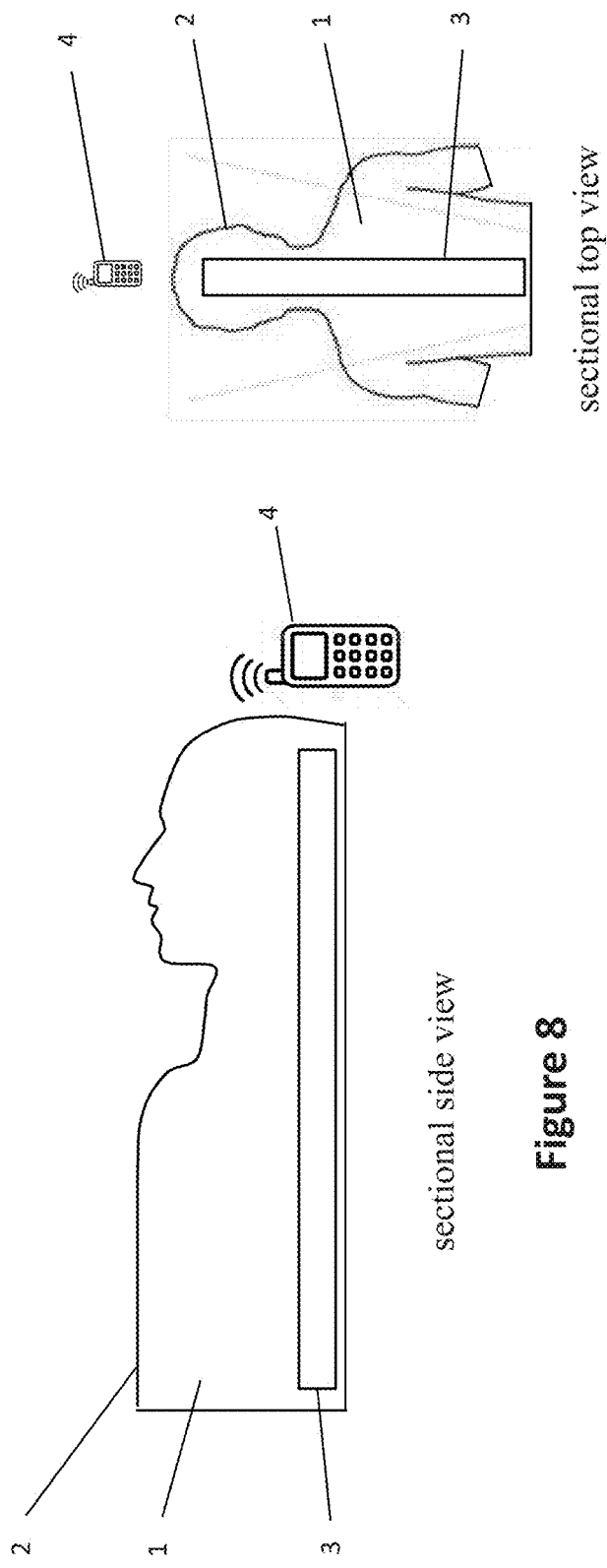

COMPOSITION SIMULATING THE DIELECTRIC PROPERTIES OF THE HUMAN BODY AND USE THEREOF FOR SAR MEASUREMENT

FIELD OF INVENTION

The present invention relates to a broadband composition simulating dielectric properties of the human body. Especially, the invention relates to a composition comprising an oil-in-water emulsion wherein the aqueous phase comprises glycerol and the oily phase comprises at least one surfactant, preferably at least two surfactants. The composition of the invention may be used to fill mannequins or phantoms used for instance in specific absorption rate (SAR) measurements, in total radiated power (TRP) measurement or total radiated sensitivity (TRS) measurement. The invention also relates to a system for measuring SAR inside a mannequin or phantom, TRP and/or TRS in proximity of a phantom, said mannequin and phantoms being filled with the broadband composition of the invention. The invention further relates to a method for SAR, TRP and/or TRS measurement comprising the use of the device of the invention.

BACKGROUND OF INVENTION

During a communication with a handheld or body-worn wireless device, biological tissues of the user are exposed to electromagnetic field energy. At frequencies used by mobile phones or other commercial devices, the radiofrequency power absorbed by the tissues is usually quantified in terms of Specific Absorption Rate (SAR).

SAR is the rate of the incremental energy (dW) absorbed by an incremental mass (dm) contained in a volume of element (dV) of a given density (ρ) when this mass is exposed to electromagnetic fields:

$$SAR = \frac{d}{dt}\left(\frac{dW}{dm}\right) = \frac{d}{dt}\left(\frac{dW}{\rho dV}\right)$$

SAR is determined by measuring the electric field distribution produced by a wireless device inside a simulated human body part containing tissue equivalent material. Limits of SAR averaged over the whole-body or locally over 1 g or 10 g of tissue (peak spatial-average) are established in international exposure guidelines/standards (ICNIRP guidelines IEEE Standard C95.1). In order to ensure the protection of public health and safety, national regulators have widely adopted such limits and recognized the use of measurement standards for assessing the peak spatial-average SAR. Measuring a wireless equipment according to the adequate SAR measurement standard (for instance IEC 62209-1 or IEC 62209-2) allows to assess the conformity of the device with regulatory requirements on human body exposure to radiofrequency field.

The measurement standards specify the use of head and body mannequins or phantoms consisting of plastic shells filled with homogeneous tissue-simulating liquids. Test configurations, phantom shapes and dielectric properties of the liquids have been designed to ensure a conservative estimate (higher value) of measured SAR compared to the SAR in a person, for a large majority of exposure conditions. Measurements of TRP and/or TRS may also require the presence of a phantom or a mannequin, as defined for example in American CTIA Test Plan for Mobile Station Over the Air Performance or in European Standard 3GPP.

FIG. 1 illustrates IEC 62209-1/62209-2 standard requirements for relative permittivity and conductivity of tissue-equivalent materials in the 0.03-6 GHz range. These dielectric properties have been defined based on studies of dielectric properties of human tissues. In vivo and in vitro measurements are reported in S. Gabriel work (Gabriel S. et al., Phys. Med. Biol., 1996, 41, 2251-2269). The choice of tissue dielectric parameters for homogeneous tissue-equivalent liquid determines the extent of any over- or underestimation when compared with SAR obtained in real-life exposure conditions. A number of studies have been carried out to verify the conservativeness of the approach (e.g. Drossos, A., Santomaa, V., and Kuster, N., "The dependence of electromagnetic energy absorption upon human head tissue composition in the frequency range of 300-3000 MHz," IEEE Transactions on Microwave Theory and Techniques, Vol. 48, No. 11, pp. 1988-1995, November 2000).

In order to achieve target dielectric characteristics, different recipes for homogeneous liquids have been proposed. Well-known solutions are for example based on water, salt and glycol (Fukunaga et al., IEEE Trans. Electromagn. Compat., 2004, 46(1), 126-129).

Such mixtures are very simple and easily obtained. However, they present the drawback of being rather narrow-band (10% to 20% relative to the central frequency). As a consequence, the fluid has to be changed several times when a device is tested in various frequency bands, leading to tedious and time-consuming manipulations. Moreover in a hermetic phantom in which a tissue simulant is embedded and cannot be changed, and if a wideband operation of this phantom-tissue arrangement is desirable, it is necessary that the contained solution delivers appropriate dielectric characteristics over a broader bandwidth.

So as to solve the above problem, several research groups have tried to develop tissue-simulating liquids usable over a wider range of frequencies.

To date, very few proposed broadband solutions exist in the art. In the knowledge of the Applicant, these solutions do not remain stable over time: dielectric properties may deviate after a few months or less; or dielectric properties do not meet standard requirements.

As a consequence, there is a need for a composition simulating dielectric properties of the human body enabling SAR measurement over a wide range of frequencies typically from 0.03 to 6 GHz, and which remains physically stable over time and wherein the dielectric properties show a very slow drift over time. Such compositions may also be used for TRP and/or TRS measurements.

The present invention solves these problems by providing a broadband composition which simulates dielectric properties over at least one decade of frequency (0.6-6 GHz). The composition of the invention contains non-toxic compounds and offers a good physical stability over time and temperature. Dielectric properties are also maintained for an increased period of time.

The invention relates to a device for SAR, TRP and/or TRS measurements, i.e. a human body part phantom filled with a composition which simulates dielectric properties over at least one decade of frequencies (0.6-6 GHz).

The invention also relates to a method for SAR measurement comprising the use of a device for SAR measurement according to the invention. The invention also relates to a method for TRP and/TRS measurement comprising the use of a device according to the invention.

The use of the broadband composition of the invention to fill phantoms used in SAR, TRP and/or TRS measurement presents the advantage of reducing measurement time since no replacement of the composition is required when changing the range of frequency. Also, this solution is suitable for being enclosed in a hermetically sealed phantom that would for instance be instrumented with an array of probes designed for measuring SAR over at least one decade of frequencies.

SUMMARY

The invention relates to an oil-in-water emulsion comprising an aqueous phase and an oily phase,
- the aqueous phase comprising water and a relaxing agent, and
- the oily phase comprising an oil and at least one surfactant.

In one embodiment, the oil-in-water emulsion of the invention has a viscosity ranging from 0.005 Pa·s to 50 Pa·s at 25° C., preferably from 0.01 Pa·s to 30 Pa·s at 25° C.

In one embodiment, the oil-in-water emulsion of the invention has a relative permittivity ranging from 68.09 to 31.2 and a conductivity ranging from 0.68 S/m to 6.60 S/m for frequencies ranging from 30 MHz to 6 GHz.

In one embodiment, the relaxing agent is a polyol, preferably glycerol.

In one embodiment, the amount of relaxing agent is ranging from 1 to 50% in weight relative to the total weight of the aqueous phase, preferably from 1% to 40%.

In one embodiment, the aqueous phase further comprises a salt, anhydrous or no anhydrous, preferably a salt selected from NaCl, $CaCl_2$ or sodium benzoate.

In one embodiment, the oil is selected from the group comprising synthetic oil such as mineral oil, paraffin oil, petroleum oil or natural oil such as lipophilic esters, triglycerides, castor oil, corn oil, olive oil, soybean oil, palm oil such as isopropyl palmitate or a mixture thereof, preferably isopropyl palmitate.

In one embodiment, the surfactant is a non-ionic surfactant selected from the group comprising poloxamers, such as triblock copolymers of ethylene oxide and propylene oxide; surfactants having polyethylene oxide and chains and at least one aromatic group such as for example Triton™-X100; sorbitan esters and ethoxylated sorbitan ester such as for example Span™80; a polysorbate such as Tween®80; polyoxyethylene alkyl ethers such as Brij® 58 or a mixture of these surfactants In one embodiment, the oil-in-water emulsion of the invention further comprises a thickening agent selected from the groups comprising alginate, xanthan, agarose, guar gum, agar, gelatin, hydroxyethylcellulose, cyclodextrines or mixtures thereof.

In one embodiment, the oil-in-water emulsion of the invention comprises:
- water,
- from 1% to 50% in weight relative to the total weight of the aqueous phase of at least one relaxing agent,
- from 0.05% to 5% in weight relative to the total weight of the emulsion of at least one salt;
- optionally a thickening agent,
- from 10% to 30% in weight relative to the total weight of the emulsion of at least one oil,
- from 5 to 10% in weight relative to the total weight of the emulsion of at least one surfactant, preferably at least two surfactants.

In one embodiment, the oil-in-water emulsion of the invention comprises:
- water,
- from 1% to 50% in weight relative to the total weight of the aqueous phase of glycerol,
- from 0.05% to 5% in weight relative to the total weight of the emulsion of $CaCl_2$;
- optionally from 0.2% to 3% in weight of the total weight of the emulsion of xanthan,
- from 10% to 30% in weight relative to the total weight of the emulsion of isopropyl palmitate,
- from 5 to 10% in weight relative to the total weight of the emulsion of a mixture of Triton X-100 and Span 80.

In one embodiment, the oil-in-water emulsion of the invention comprises:
- water,
- from 15% to 35% in weight relative to the total weight of the aqueous phase of glycerol,
- from 0.6% to 1.2% in weight relative to the total weight of the emulsion of $CaCl_2$;
- optionally from 0.3% to 2% in weight of the total weight of the emulsion of xanthan,
- from 15% to 25% in weight relative to the total weight of the emulsion of isopropyl palmitate,
- from 6 to 8% in weight relative to the total weight of the emulsion of a mixture of Triton X-100 and Span 80 preferably in a ratio Triton X-100/Span 80 of 79/21.

In one embodiment, the oil-in-water emulsion of the invention comprises:
- water,
- from 2% to 7% in weight relative to the total weight of the aqueous phase of glycerol,
- from 0.1% to 1% in weight relative to the total weight of the emulsion of $CaCl_2$;
- optionally from 0.3% to 2% in weight of the total weight of the emulsion of xanthan,
- from 10% to 15% in weight relative to the total weight of the emulsion of isopropyl palmitate,
- from 6 to 8% in weight relative to the total weight of the emulsion of a mixture of Triton X-100 and Span 80 preferably in a ratio Triton X-100/Span 80 of 79/21.

The present invention further relates to a device comprising:
- an emulsion according to the invention,
- a simulated human body part filled with said emulsion; and
- at least one system capable of measuring a local specific absorption rate when the simulated human body part is exposed to an electromagnetic field.

In an embodiment, the simulated human body part is a container in the form of part or all of a human head or part or all of a human trunk.

The invention further relates to a method for conducting specific absorption rate tests of an apparatus radiating an electromagnetic field comprising:
- positioning the apparatus on or near, preferably in close vicinity to, a device according to the invention;
- measuring a field strength within the device when the apparatus under test is transmitting.

The invention also relates to a process of manufacturing an emulsion according to the invention, comprising:
- dissolving the thickening agent, when applicable, in water under stirring to give composition (I);
- dissolving the salt, when applicable, in water under stirring and adding the relaxing agent under stirring to give composition (II);

mixing compositions (I) and (II) to form the aqueous phase;

dissolving the surfactants in the oil under stirring to form the oily phase;

dispersing the oily phase in the aqueous phase under stirring;

wherein the process is performed at a temperature ranging from 20° C. to 25° C.

DEFINITIONS

In the present invention, the following terms have the following meanings:

"about" preceding a figure means plus or less 10% of the value of said figure.

"relaxing agent" refers to a chemical compound capable of inducing additional relaxation processes to the system comprising it. In the present invention, relaxing agents are preferably polyols such as for example glycerol.

"relative permittivity" is as defined in the Standard IEEE1528 (2003).

"conductivity" is as defined in the Standard IEEE1528 (2003).

"low frequency", in the meaning of the present invention, refers to frequencies ranging from about 30 MHz to about 2 GHz.

"viscosity" refers to dynamic viscosity.

"polyol" refers to a chemical compounds comprising at least two —OH functions.

"thickening agent" relates to a chemical compound capable of increasing the viscosity of a composition.

"simulated human body part" refers to a container in the form of part or all of a human body, such as for example a mannequin or a phantom. Such mannequins or phantoms are commonly used in SAR measurements.

"cloud point" refers to the temperature above which the solubility of surfactants in water is affected and the mixture starts to separate.

DETAILED DESCRIPTION

Composition

The present invention relates to a composition simulating dielectric properties of at least one part of the human body, preferably the head or trunk. The composition of the invention is a broadband product. In the meaning of the present invention broadband refers to at least one decade of frequency, preferably from 10 MHz to 10 GHz, more preferably from 30 MHz to 6 GHz or from 600 MHz to 6 GHz.

The composition of the invention comprises a direct oil-in-water emulsion wherein:

the aqueous phase comprises water and a relaxing agent; and the oily phase comprises an oil and at least one surfactant.

In an embodiment, the composition of the invention comprises a direct oil-in-water emulsion wherein:

the aqueous phase comprises water and glycerol; and the oily phase comprises an oil and at least one surfactant, preferably at least two surfactants.

In an embodiment, the composition of the invention comprises a direct oil-in-water emulsion wherein:

the aqueous phase comprises water and a relaxing agent; and the oily phase comprises an oil and at least one surfactant, preferably at least two surfactants;

said emulsion having a viscosity ranging from 0.005 Pa·s to 50 Pa·s at 25° C., preferably from 0.01 Pa·s to 30 Pa·s at 25° C.

Aqueous Phase

According to an embodiment, the aqueous phase of the emulsion comprises water, deionized water, demineralized water, an aqueous solution such as for example salted water, or a mixture thereof.

In an embodiment, the relaxing agent is a polyol, such as for example glycerol or a sugar, preferably glycerol.

According to a first embodiment, the relaxing agent is glycerol.

According to a second embodiment, the relaxing agent is a sugar such as for example a monosaccharide such as fructose, a disaccharide such as saccharose, or a mixture thereof.

According to a particular embodiment, the relaxing agent is not a sugar, especially not a monosaccharide or a disaccharide. In a specific embodiment, the emulsion of the invention does not comprise monosaccharides or disaccharides.

In an embodiment, the aqueous phase comprises an amount of relaxing agent ranging from 1% to 50% in weight relative to the total weight of the aqueous phase (w/w aqueous phase), preferably from 1% to 40% w/w aqueous phase.

In a first embodiment, the aqueous phase comprises an amount of relaxing agent, preferably glycerol, ranging from 10% to 40% w/w aqueous phase, preferably from 15% to 35% w/w aqueous phase, more preferably from 17% to 25% w/w aqueous phase, more preferably from 19% to 21% w/w aqueous phase even more preferably about 20% w/w aqueous phase. Preferably, the amount of relaxing agent is such that the relative permittivity of the emulsion ranges from 60.5 to 31.2 for frequencies ranging from 30 MHz to 6 GHz.

In a second embodiment, the aqueous phase comprises an amount of relaxing agent, preferably glycerol, ranging from 1% to 10% w/w aqueous phase, preferably from 2% to 7% w/w aqueous phase, more preferably from 2% to 5% w/w aqueous phase, even more preferably about 3% w/w aqueous phase. Preferably, the amount of relaxing agent is such that the relative permittivity of the emulsion ranges from 68.09 to 43.38 for frequencies ranging from 0.15 GHz to 6 GHz.

The amount of relaxing agent may be adapted to obtain the dielectric properties required by standards for tissue-simulating materials.

In one embodiment, the aqueous phase is essentially composed of deionized water and 20% of polyol, preferably glycerol.

In the present invention, the use of a relaxing agent enables tuning the complex permittivity of the composition in a given range of frequencies. Polyols, and especially glycerol, as relaxing agent, present the advantage not much affecting the relative permittivity of the composition. Moreover, and without willing to be bound by a theory, it is the Applicant understanding that polyols participate to obtain a range of working temperature from about 20 to about 40° C., preferably the working temperature is ambient temperature.

In an aspect of the invention, the aqueous phase further comprises a salt. Different salts may be used at various amounts depending on their composition. The amount of salt may be determined by experience and calculations. In an embodiment, salt is chosen among the group comprising NaCl, $CaCl_2$, sodium benzoate or a mixture therefore. Salts may be anhydrous or not anhydrous. In an embodiment, the amount of salt is ranging from 0.05% to 5% in weight relative to the total weight of the emulsion (w/w), preferably from 0.1% to 2.5% w/w. In an embodiment, the salt is $CaCl_2$, preferably anhydrous $CaCl_2$ and is used in amounts ranging from 0.1% to 5% in weight relative to the total weight of the emulsion (w/w), preferably from 0.4% to 2.5% w/w, more preferably from 0.6% to 1.2% w/w. In a preferred embodiment, the salt is $CaCl_2$, preferably anhydrous $CaCl_2$ and is used in amounts ranging from 0.6% to 1.2 w/w, preferably from 0.9% to 1.1% w/w. In another preferred embodiment, the salt is $CaCl_2$, preferably anhydrous $CaCl_2$ and is used in amounts ranging from 0.1% to 1.0 w/w, preferably from 0.5% to 0.8% w/w. Preferably, the amount of salt is such that the conductivity of the emulsion, at low frequency is higher than 0.68 S/m, preferably ranges from 0.68 S/m to 6.60 S/m for frequencies ranging from 0.03 GHz to 6 GHz.

The presence of a salt advantageously enables to reach values of conductivity determined by the standard. It is the Applicant's understanding that the presence of a salt in the aqueous phase does not affect significantly, in the ranges of the present invention, the relative permittivity of the emulsion.

Oily Phase

According to one embodiment, the oil may be a synthetic oil such as for example a mineral oil, paraffin oil or petroleum oil, a natural oil such as for example liphophilic esters, triglycerides, castor oil, corn oil, olive oil, soybean oil, palm oil or a mixture thereof. In preferred embodiment, the oil is a palm oil, preferably isopropyl palmitate. In another embodiment, the oil is a non-vegetal oil.

According to one embodiment, the amount of oil in the emulsion of the invention is ranging from 10% to 30% in weight relative to the total weight of the emulsion (w/w). In a preferred embodiment, the amount of oil in the emulsion of the invention is ranging from 15 to 25% w/w, preferably from 17% to 19% w/w. In another preferred embodiment, the amount of oil in the emulsion of the invention is ranging from 10 to 15% w/w, preferably from 12.5% to 14% w/w.

In one embodiment, the oily phase comprises at least one non-ionic surfactant, anionic surfactant, cationic surfactant or zwitterionic surfactant. Non-ionic surfactants may be for example a poloxamer, such as triblock copolymers of ethylene oxide and propylene oxide, for example Pluronic® products marketed by BASF, surfactants having polyethylene oxide and chains and at least one aromatic group, such as for example a Triton-X100 marketed by Union Carbide; sorbitan esters and ethoxylated sorbitan ester such as for example Span™80 marketed by Croda or a polysorbate such as Tween® 80 marketed by Sigma-Aldrich, polyoxyethylene alkyl ethers such as Brij®58 marketed by Sigma-Aldrich or a mixture of these surfactants. Anionic surfactants may be for example anionic lipids such as phospholipids; or sodium dodecyl sulfate SDS. Cationic surfactants may be for example quaternary ammonium compounds such as hexadecyltrimethylammonium bromide CTAB; primary amine such as oleyamine or stearylamine; cationic lipids; chlorhexidin salts; or cationic polymers such as chitosan. Zwitterionic surfactants may be for example lecithin.

According to a preferred embodiment, the oily phase comprises at least one non-ionic surfactant.

According to a preferred embodiment, the oily phase comprises a mixture of at least two surfactants, preferably at least two non-ionic surfactants. It is especially preferred that the oily phase comprises a mixture of two surfactants having different hydrophilicities.

The use of a mixture of two non-ionic surfactants presents the advantage to increase the stability of the emulsion.

Preferred combination of non-ionic surfactants is Triton-X100/Span 80 or Tween80/Span 80, but other mixtures may be considered.

In one embodiment, the total amount of surfactants in the emulsion is ranging from 5 to 10% in weight relative to the total weight of the emulsion (w/w), preferably from 6% to 8% w/w.

Viscous Composition

Advantageously, the emulsion of the invention is a viscous composition. This is especially interesting for phantom filling concerns and limits leakage risks. Moreover, the viscosity of the composition participates to the physical stability of the emulsion.

According to one embodiment, the emulsion of the invention presents a viscosity ranging from 0.005 Pa·s to 50 Pa·s at 25° C., preferably from 0.01 Pa·s to 30 Pa·s at 25° C.

The viscosity of the emulsion of the invention may be measured using a Low Shear LS 400 (Lamy Rheology) of Couette type, in the case of Newtonian fluids. The viscosity may also be measured using a HAAKE RheoStress 600 rheometer, with cone-plate geometry, in the case of non-Newtonian fluids.

A composition with such a viscosity was found by the Applicant to be well adapted to the filling of simulated body parts, especially those with complex shapes, without introducing air pocket or air bubbles therein.

According to an embodiment, the relaxing agent of the emulsion further acts as a viscosifying agent. This is especially the case when the relaxing agent is glycerol.

According to another embodiment, the emulsion of the invention may further comprise a thickening agent to reach intended viscosities.

In one embodiment, the thickening agent is for example, hydrocolloids and especially different polysaccharides such as alginate, xanthan, agarose, guar, agar, gelatin, hydroxycellulose, cyclodextrines or mixtures thereof. In a preferred embodiment, the thickening agent is xanthan or agarose. Preferably, the thickening agent may be incorporated in the emulsion of the invention at ambient temperature.

In an embodiment, thickening agents are used in typical amounts ranging from 0.2% to 3% in weight of the total weight of the emulsion (w/w), preferably from 0.3% to 2% w/w, more preferably from 0.4% to 0.6% w/w.

Further Components

According to one embodiment, the emulsion of the invention may further comprise additives such as Vitamin E as anti-oxidant.

According to an embodiment, the emulsion of the invention further comprises a preservative agent and/or a bactericidal agent, such as for example sodium azide or Germaben II (Lotion Crafter).

Dielectric Properties

The emulsion of the invention is a broadband tissue-simulating composition.

In one aspect of the invention, the emulsion has a relative permittivity ranging from 60.5 to 31.2 for frequencies ranging from 30 MHz to 6 GHz. In another aspect of the invention, the emulsion has a relative permittivity ranging from 68.09 to 43.38 for frequencies ranging from 0.15 GHz to 6 GHz. In another aspect of the invention, the emulsion has a relative permittivity ranging from 68.09 to 31.2 for frequencies ranging from 0.03 GHz to 6 GHz. In a preferred embodiment, the emulsion has a relative permittivity within the range set forth by the International Electrotechnical Commission (IEC) under the reference IEC 62209-1/2 with tolerated +/−10% deviations. In another preferred embodiment, the emulsion has a relative permittivity within the range set forth by the American Federal Communications Commission (FCC) under the reference OET Bulletin 65 Supplement C with +/−10% deviations and preferably with +/−5% deviations.

In one aspect of the invention, the emulsion has a conductivity ranging from 0.68 S/m to 6.03 S/m for frequencies ranging from 30 MHz to 6 GHz. In another aspect of the invention, the emulsion has a conductivity of more than 0.72 S/m, preferably ranging from 0.72 S/m to 6.60 S/m for frequencies ranging from 150 MHz to 6 GHz. In another aspect of the invention, the emulsion has a conductivity ranging from 0.68 S/m to 6.60 S/m for frequencies ranging from 30 MHz to 6 GHz. In a preferred embodiment, the emulsion has a conductivity within the range set forth by the International Electrotechnical Commission (IEC) under the reference IEC 62209-1/2 with tolerated +/−10% deviations. In another preferred embodiment, the emulsion has a conductivity within the range set forth by the American Federal Communications Commission (FCC) under the reference OET Bulletin 65 Supplement C with +/−10% deviations and preferably with +/−5% deviations.

Relative permittivity and conductivity may be measured using the 85070 E dielectric probe kit from Agilent Technologies together with a vector network analyzer.

According to an embodiment, the emulsion of the invention meets standard requirements defined by the International Electrotechnical Commission (IEC) under the reference IEC 62209-1/2 with tolerated +/−10% deviations.

According to an embodiment, the emulsion of the invention approaches target dielectric parameter values defined by the American Federal Communications Commission (FCC) under the reference OET Bulletin 65 Supplement C with +/−10% deviations and preferably with +/−5% deviations.

Droplets Size

According to one embodiment, oil droplets of the oil-in-water emulsion of the invention have a mean size ranging from 80 nm to 50 µm, preferably from 200 nm to 30 µm.

Stability of the Composition

The assessment of the stability of the emulsion may comprise assessing the physical stability of the emulsion over time. In a specific embodiment, the physical stability of the emulsion may be evaluated by visual estimation of phase separation overtime and/or by measuring the droplets size overtime. The measurement of droplet size may be achieved by DLS (Dynamic light scattering) or optical and electronic microscopy.

In an embodiment, the emulsion of the invention remains physically stable for a period of time of more than 6 months, preferably more than 9 months, more preferably more than one year, even more preferably more than three years.

The assessment of the stability of the emulsion may also comprise assessing the stability overtime of the dielectric properties of the emulsion. In a specific embodiment, the emulsion meets standard requirement defined by the International Electrotechnical Commission under the reference IEC 62209-1/IEC 62209-2 with tolerated +/−10% deviations for at least 6 months, preferably at least 9 months, more preferably at least one year, even more preferably more than three years. In another specific embodiment, the emulsion meets regulatory requirements defined by the American Federal Communications Commission (FCC) under the reference OET Bulletin 65 Supplement C with +/−10% deviations for at least 6 months, preferably at least 9 months, more preferably at least one year, even more preferably more than three years.

The assessment of the stability of the emulsion may also comprise assessing the bacterial and microbial stability of the emulsion overtime. In a specific embodiment, the bacterial and microbial stability of the emulsion may be evaluated by visual determination of mold growth.

Process of Manufacturing of the Composition of the Invention

During the manufacturing of the emulsion of the invention, it may be important to control the speed of stirring and the temperature of the mixture for the stability of the resulting emulsion.

In one embodiment of the invention, the method for manufacturing the emulsion of the invention comprises:
  dissolving the thickening agent, when applicable, in water under stirring to give composition (I);
  dissolving the salt, when applicable, in water under stirring, adding the relaxing agent under stirring and optionally a preservative agent, to give composition (II);
  mixing compositions (I) and (II);
  dissolving surfactants in oil under stirring;
  dispersing the oily phase in the aqueous phase under stirring.

In an embodiment, the stirring is performed using a propeller stirrer, a paddle stirrer, a turbine, a colloidal mill, an ultra turrax, ultrasounds using for example an ultrasounds stick, preferably an propeller stirrer or a paddle stirrer, the paddle stirrer being optionally associated with a turbine.

During the process, the temperature is advantageously maintained between 20° C. and 25° C., preferably at room temperature. Working at ambient temperature is highly desirable from an industrial point of view to save costs of production but also for stability concerns as emulsions may not be stable at elevated temperature. Moreover, dielectric properties may be affected by elevated temperatures.

In another embodiment, some steps of the process may be performed at a temperature ranging from 20° C. to 70° C., preferably at about 35° C., especially the step of dissolution of the thickening agent.

It is important to choose the type of stirring, the speed, the temperature and the duration so that the cloud point of the used surfactants, especially non-ionic surfactants, is not exceeded. The use of an ice bath would therefore be important when using an ultrasounds stick, since ultrasounds lead to the heating of the sample.

Device for SAR, TRP and/or TRS Measurements

The present invention further relates to a device for SAR measurement comprising the emulsion of the invention. The present invention further relates to a device for TRP and/or TRS measurement comprising the emulsion of the invention.

The invention relates to a simulated human body part filled with the emulsion of the invention described above. By "filled", it is meant totally filled, i.e. without remaining air pockets or air bubbles.

The invention also relates to a device comprising:
  an emulsion according to the invention;
  a simulated human body part filled with said emulsion;
  at least one system capable of measuring a local specific absorption rate when the simulated human body part is exposed to an electromagnetic field.

In a preferred embodiment, the simulated human body part is hermetically sealed.

In an aspect of the invention, the simulated human body part is made of plastic shells, preferably rigid plastic shells.

According to an embodiment, the shape of the simulated human body part may be a head, a hand, a trunk or a part thereof and/or a combination thereof. Preferably, the shape of the simulated human body part meets requirements defined by IEC and IEEE standards.

In an embodiment, the emulsion of the invention is filled within the simulated human body part in a manner such as introduction of air bubbles or air pocket is limited if not completely avoided. Indeed, air bubbles should be avoided when filing the phantom with the composition otherwise it would impact dielectric properties of the phantom. Especially, no air pocket should be present in the phantom during the SAR, TRP and/or TRS measurement otherwise erroneous values could be obtained. This is especially a concern if the air pocket is located close to where the apparatus to be tested should be placed.

In a preferred embodiment, the simulated human body part is filled with the emulsion under vacuum.

According to an embodiment, the system for measuring SAR includes a probe, which may be for example a single diode-detected probe capable of assessing the squared amplitude of the electric field. In an embodiment, the probe may be an array of single diode-detected probes. In a preferred embodiment the probe may be a single or an array of probes capable of assessing vector electric field. An array of vector probes could be as the one defined in Patent Application WO 2011/080332.

Advantageously, the probe comprises a measuring part and a connective part, wherein the measuring part is located within the simulated human body part and the connective part is located outside the simulated human body part. The probe may be connected, through its connective part to a multiplexing stage, followed by a downconverting stage, followed by a analog-to-digital converter, followed by a processing unit. It may generally be connected to a readout electronic part. Advantageously, the probe is coated with a conformal coating or any suitable varnish.

Measurement Methods

The present invention further relates to a method of SAR measurement comprising the use of the emulsion of the invention. In an embodiment, the method of SAR measurement comprises the use of a simulated human body part comprising the emulsion of the invention, preferably the device of the present invention.

According to an embodiment, the method for conducting specific absorption rate tests of an apparatus radiating an electromagnetic field, such as a communication device, comprises:
  positioning the apparatus on or near, preferably in close vicinity to, a device according to the invention,
  measuring a field strength within the simulated human body part when the apparatus under test is transmitting.

In an embodiment, the method further comprises a signal processing stage to evaluate the 3-D distribution of specific absorption rate and finally obtain the peak spatial-average SAR.

The present invention further relates to a method of TRP and/or TRS measurement comprising the use of the emulsion of the invention. In an embodiment, the method of TRP and/or TRS measurement comprises the use of a simulated human body part comprising the emulsion of the invention, preferably the device of the present invention. In a preferred embodiment, the method of TRP and/or TRS measurement of the invention meets requirements from CTIA and/or 3GPP.

BRIEF DESCRIPTION OF THE DRAWINGS

FIG. 8 is a sectional side view of a device of the invention showing a simulated human body (2) filled by an emulsion of the invention (1), a system capable of measuring the local specific absorption rate (3) when the simulated human body part is exposed to an electromagnetic field, and an apparatus radiating an electromagnetic field (4).

FIG. 9 is a sectional top view of a device of the invention showing a simulated human body (2) filled by an emulsion of the invention (1), a system capable of measuring the local specific absorption rate (3) when the simulated human body part is exposed to an electromagnetic field, and an apparatus radiating an electromagnetic field (4).

EXAMPLES

The present invention is further illustrated by the following examples.

Unless otherwise specified, percentages are given in weight relative to the total weight of the composition.

General Method of Dielectric Properties Measurement

An open-ended coaxial dielectric probe from Agilent Technologies (85070E) was used. This widely-used technique has the advantage to be easy-to-use, available to everyone and applicable up to 6 GHz.

Measurements were carried out with a temperature of the sample under test varying from 20° C. to 40° C., preferably at 25° C.

EXAMPLE 1

Standard Compositions of the Invention

Formulation:

| Composition | Emulsion 1 | Emulsion 2 |
|---|---|---|
| water | 57.21% | 56.48% |
| glycerol | 14.57% | 14.08% |
| anhydrous $CaCl_2$ | 1.13% | 1.11% |
| isopropyl palmitate | 19.89% | 20.39% |
| Triton X-100/Span 80 (79:21) | 7.20% | \ |
| Tween 80/Span 80 (67:33) | \ | 7.94% |

Process of Manufacturing:

The following steps were followed to manufacture above exemplified emulsions 1 and 2.

1) aqueous phase:
weighting of water, glycerol and anhydrous CaCl2;
stirring with a propeller stirrer of the mixture to dissolve CaCl2 on a water-bath at 35° C.;

2) oily phase:
weighting of oil, Triton X100 or Tween 80 and Span 80;
stirring with a propeller stirrer of the mixture to solubilize oil and surfactants, on water bath at 35° C.;

3) emulsification
the oily phase is added in the aqueous phase under propeller stirring, on water bath at 35° C.;
the mixture is stirred at 600 r/min for 45 minutes;

4) transferring of the resulting emulsion in a closed bottle, at room temperature;

5) the emulsion is then submitted to ultrasounds emitting a power of 30 W in continuous for 1 hour, using an ultrasounds stick plunged in the bottle, on an ice bath to avoid heating of the composition.

Emulsions 1 and 2 have a viscosity of about 6 cP at 25° C.

Figure 1:
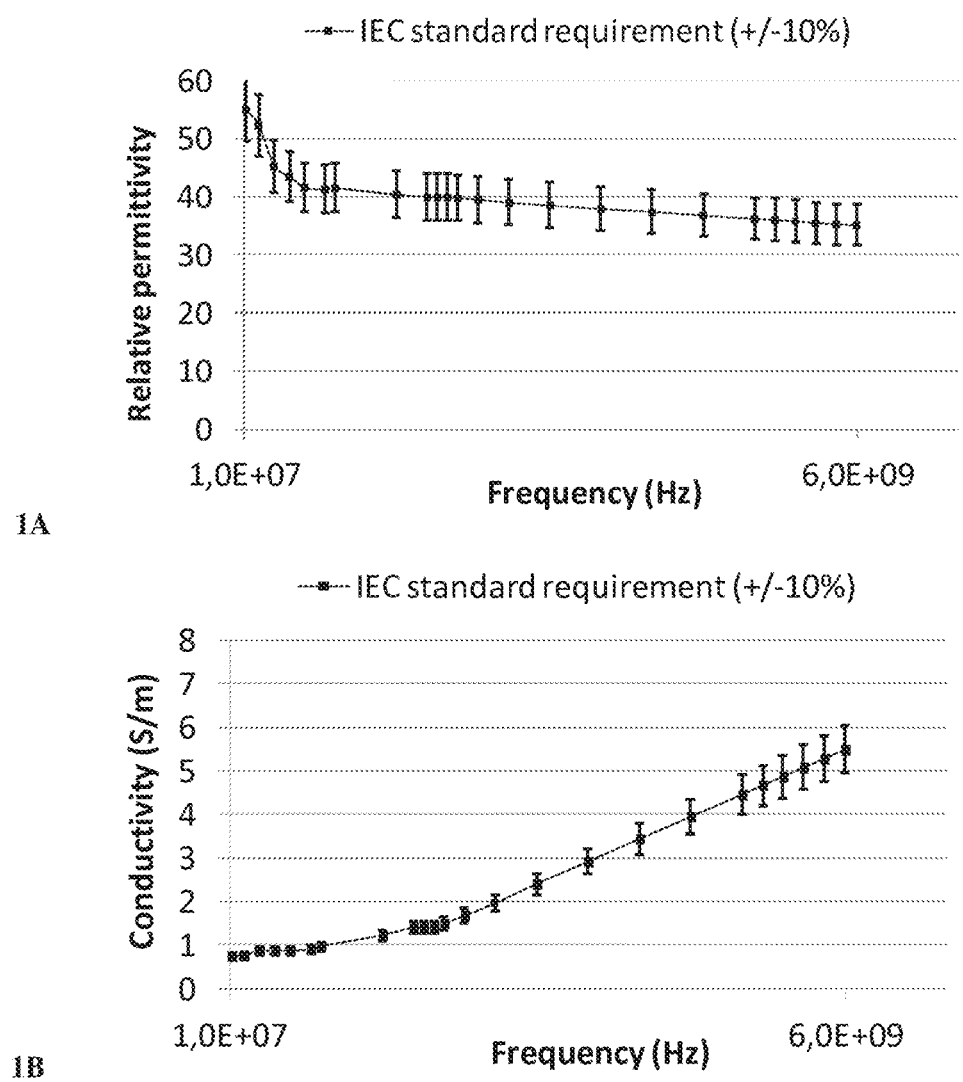
FIG. 1 illustrates the IEC 62209-2 standard requirement for tissue-simulating dielectric properties materials with tolerated +/−10% deviations in the 0.03-6 GHz range. (1A) represents the relative permittivity of the material as a function of the frequency. (1B) represent the conductivity of the material as a function of the frequency.
Figure 2:
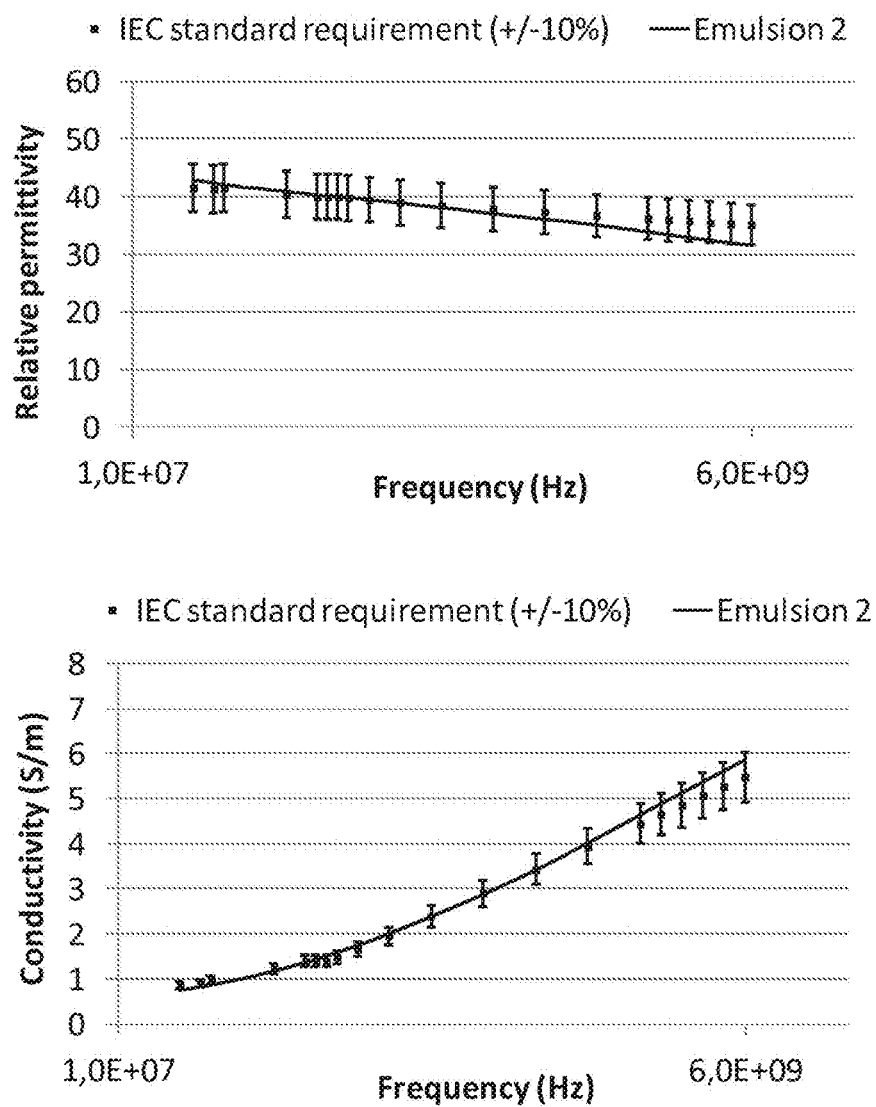
FIG. 2 represents the dielectric properties of emulsion 2 of example 1 compared to IEC standard requirements with tolerated +/−10% deviations, from 0.6 GHz to 6 GHz.

Dielectric Properties Measurement:

The dielectric properties of exemplified emulsions 1 and 2 were measured using the general method described above. Results are presented in FIG. 2, showing that emulsions meet IEC standards requirements with tolerated +/−10% deviations.

Stability:

Dielectric properties are stable for at least 1.5 year.

EXAMPLE 2

Thickened Compositions—Xanthan

Formulation:

| Composition | Emulsion 3 | Emulsion 4 | Emulsion 5 |
|---|---|---|---|
| water | 56.95% | 57.10% | 58.79% |
| glycerol | 14.69% | 14.60% | 14.50% |
| anhydrous CaCl$_2$ | 1.08% | 1.10% | 1.04% |
| xanthan | 0.65% | 0.60% | 0.56% |
| Germaben II | \ | \ | 0.34% |
| isopropyl palmitate | 19.67% | 19.70% | 18.78 |
| Triton X-100/Span 80 (79:21) | 6.96% | \ | 6.09% |
| Tween 80/Span 80 (67:33) | \ | 6.90% | \ |

Process of Manufacturing:

The following steps were followed to manufacture above exemplified emulsions 3, 4 and 5:

1) aqueous phase:
weighting of water, glycerol and anhydrous CaCl2;
stirring with a propeller stirrer of the mixture to dissolve CaCl2 on a water-bath at 35° C.;
heating of the water bath at 70° C.;
addition of the xanthan powder in rain under mechanical stirring (300 r/min) for 5 minutes;
the aqueous phase is then brought back to 35° C. by decreasing the temperature of the water bath;

2) oily phase:
weighting of oil, Triton X100 or Tween 80 and Span 80;
stirring with a propeller stirrer of the mixture to well solubilize oil and surfactants, on water bath at 35° C.;

3) emulsification
the oily phase is added in the aqueous phase under stirring with a propeller stirrer, on a water bath at 35° C.;
the mixture is stirred at 600 r/min for 45 minutes;

4) transferring of the resulting emulsion in a closed bottle, at room temperature.

All the step of above process of manufacturing may also be performed at 25° C.

Emulsions 3, 4 and 5 have a viscosity of about 30 Pa·s at 25° C.

Figure 3:
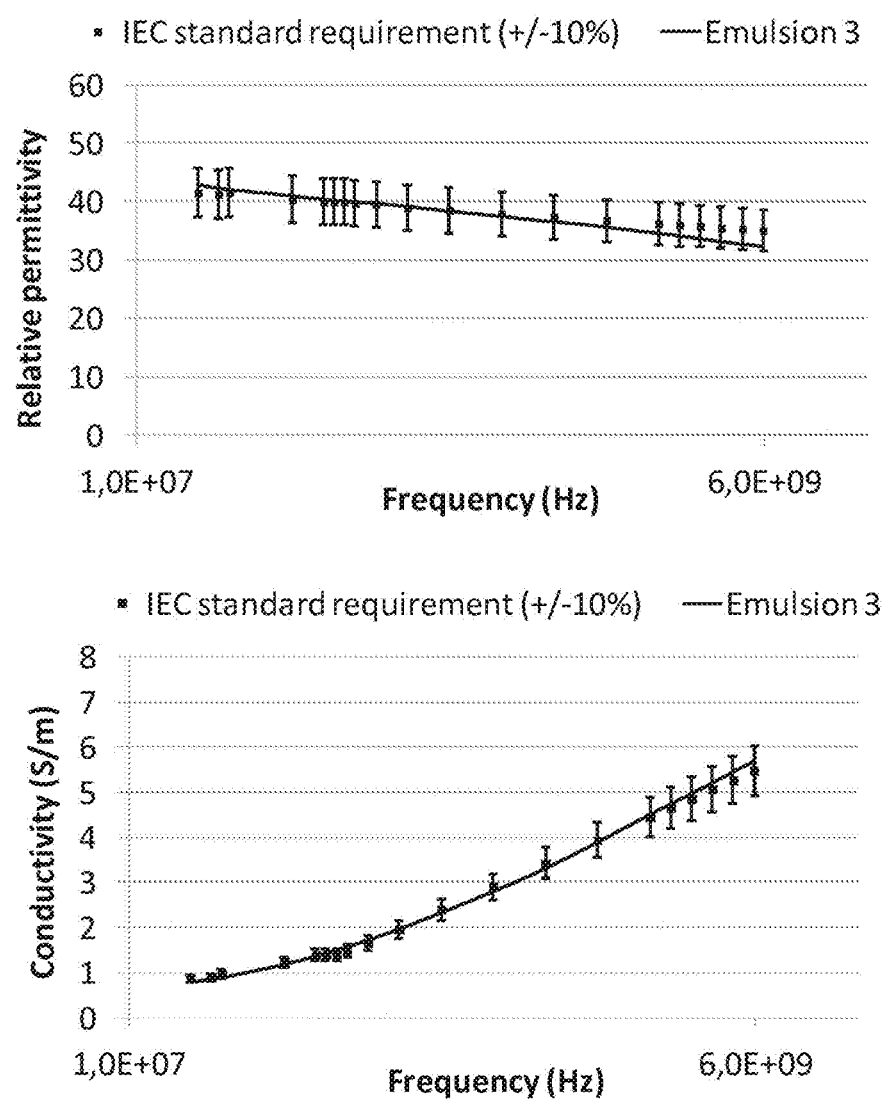
FIG. 3 represents the dielectric properties of emulsion 3 of example 2 compared to IEC standard requirements with tolerated +/−10% deviations, from 0.6 GHz to 6 GHz.
Figure 4:
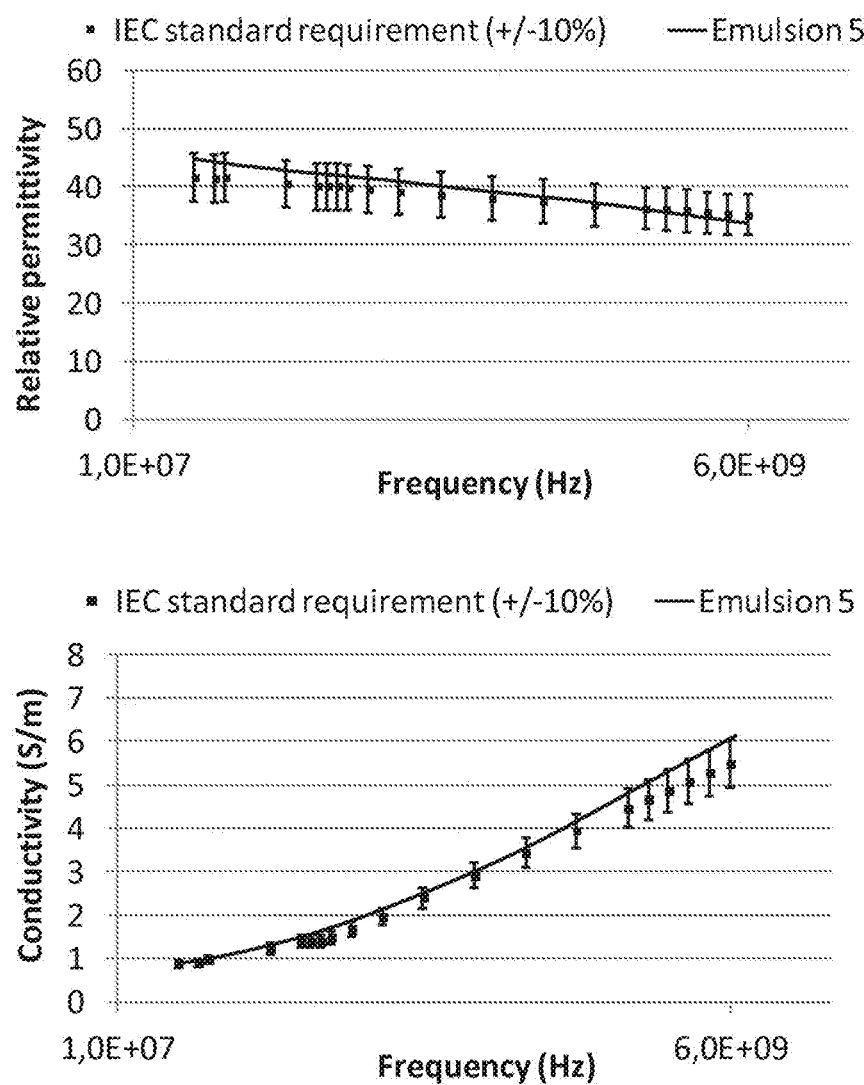
FIG. 4 represents the dielectric properties of emulsion 5 of example 2 compared to IEC standard requirements with tolerated +/−10% deviations, from 0.6 GHz to 6 GHz.

Dielectric Properties Measurement:

The dielectric properties of exemplified emulsions 3 and 5 were measured using the general method described above. Results are presented in FIG. 3 and FIG. 4 respectively (0.6 GHz to 6 GHz), showing that emulsions 3 and 5 meet IEC standards requirements with tolerated +/−10% deviations.

Figure 5:
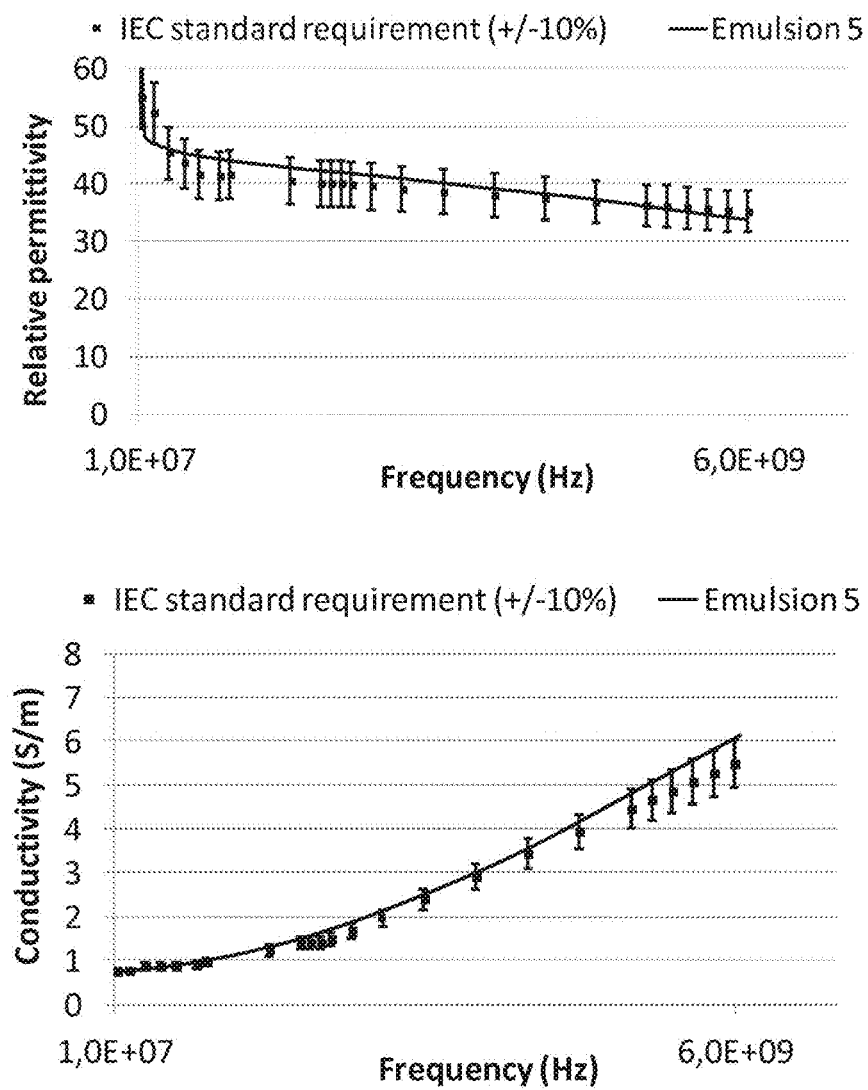
FIG. 5 represents the dielectric properties of emulsion 5 of example 2 compared to IEC standard requirements with tolerated +/−10% deviations, from 0.03 GHz to 6 GHz.

Emulsion 5 has also interesting dielectric properties on a larger band of frequencies, from 0.03 GHz to 6 GHz (see FIG. 5).

Stability:

Dielectric properties are stable for at least 1 year.

EXAMPLE 3

Thickened Compositions—Agarose

Formulation:

| Composition | Emulsion 6 |
|---|---|
| water | 59.90% |
| glycerol | 15.03% |
| anhydrous CaCl$_2$ | 0.84% |
| agarose | 2.10% |
| isopropyl palmitate | 14.49% |
| Tween 80/Span 80 (70:30) | 7.64% |

Process of Manufacturing:

The following steps were followed to manufacture above exemplified emulsion 6:

1) aqueous phase:
weighting of water, glycerol and anhydrous CaCl2;
stirring with a propeller stirrer of the mixture to dissolve CaCl2 on a water-bath at 35° C.;
changing the water-bath to an oil bath at 80° C.;
addition of the agarose powder in rain under stirring with a propeller stirrer for 5 minutes;

2) oily phase
weighting of oil, Tween 80 and Span 80;
stirring with a propeller stirrer of the mixture to well solubilize oil and surfactants, on oil bath at 80° C.;

3) emulsification
the oily phase is added in the aqueous phase under stirring with a propeller stirrer, on an oil bath at 80° C. for 5 minutes;
the mixture is stirred at 600 r/min at 35° C. for 30 minutes;

4) transferring of the resulting emulsion in a closed bottle, at room temperature.

EXAMPLE 4

Evolution of Dielectric Properties with Temperature

Dielectric properties of emulsion 5 of example 2 were studied in function of the temperature of the emulsion.

Figure 6:
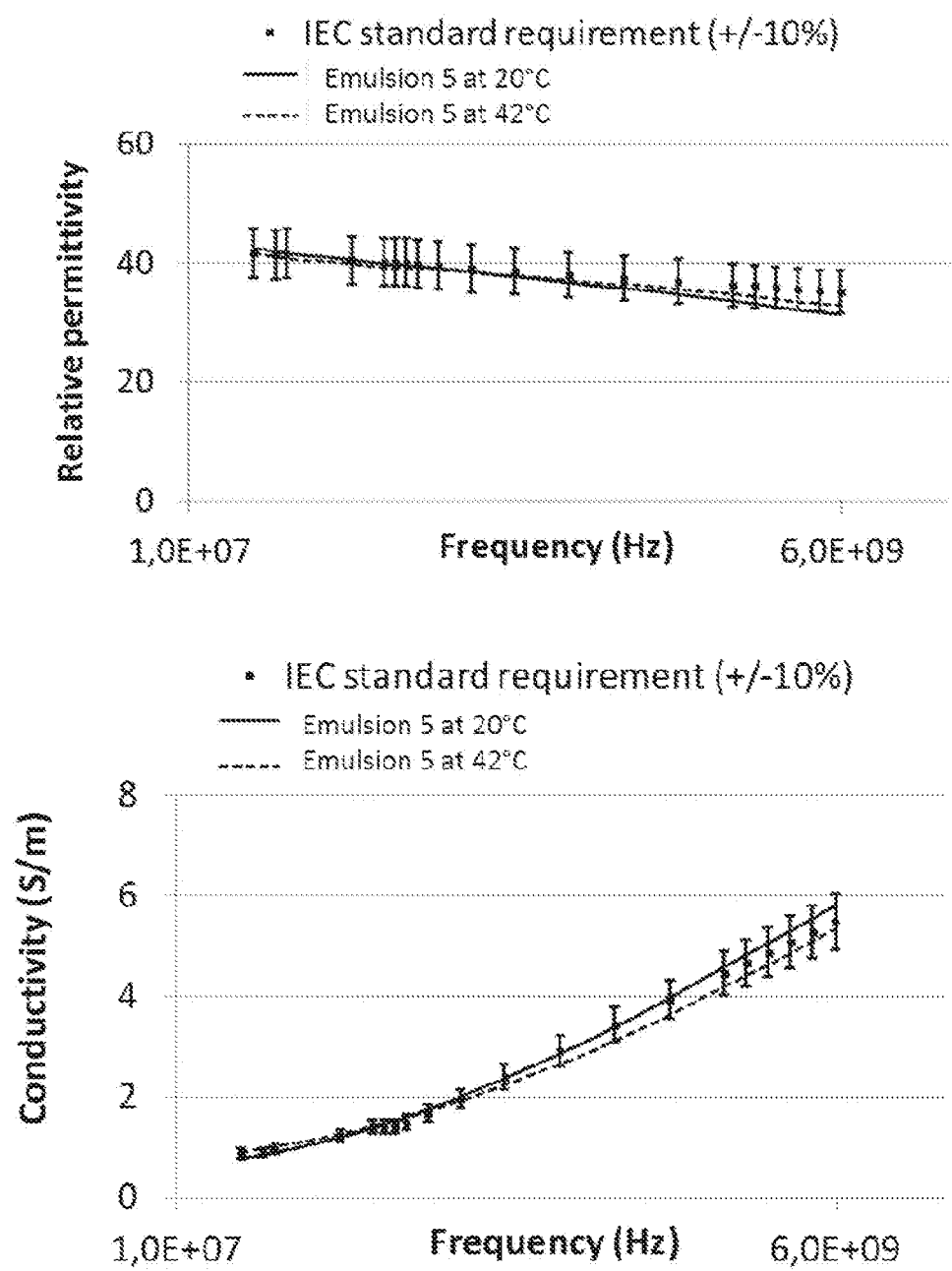
FIG. 6 represents the dielectric properties of emulsion 5 of example 2 at 20° C. and 42° C. compared to IEC standard requirements with tolerated +/−10% deviations, from 0.6 GHz to 6 GHz.

Between 20 to 40° C., dielectric properties required by IEC standards are maintained as evidenced on FIG. 6.

The emulsion can be used from 20° C. to 40° C. during a certain time, according to the limitations of the temperature dependence emulsion stability. The emulsion will be preferably used between 25° C. and 30° C.

EXAMPLE 5

Study of the Rheological Properties of the Composition

Rheological properties of emulsion 5 of example 2 were studied. Measures were performed on emulsion, at 25° C., with a HAAKE RS600 rheometer, with a cone-plate geometry.

Emulsion 5 has a viscosity of about 30 Pa·s at 25° C.

Emulsion 5 was found to be a rheofluidizing, thixotropic and plastic fluid. A fluid with such rheological properties is easy to manipulate, enables the filling of the simulated human body part and limits, if any, leakage of the fluid.

EXAMPLE 6

Composition Approaching American FCC Regulatory Target Values

Emulsions of above examples meet standard requirement defined by the International Electrotechnical Commission under the reference IEC 62209-2 with tolerated +/−10% deviations.

Compositions reaching the FCC (Federal Communications Commission) American regulatory requirements may also be interesting for SAR measurement.

Formulation:

| Composition | Emulsion 7 |
|---|---|
| water | 76.66% |
| glycerol | 2.69% |
| anhydrous CaCl$_2$ | 0.63% |
| isopropyl palmitate | 12.87% |
| Triton X100/Span 80 (79:21) | 7.16% |

Emulsion 7 was manufactured according to the same process as Emulsions 1 and 2.

Figure 7:
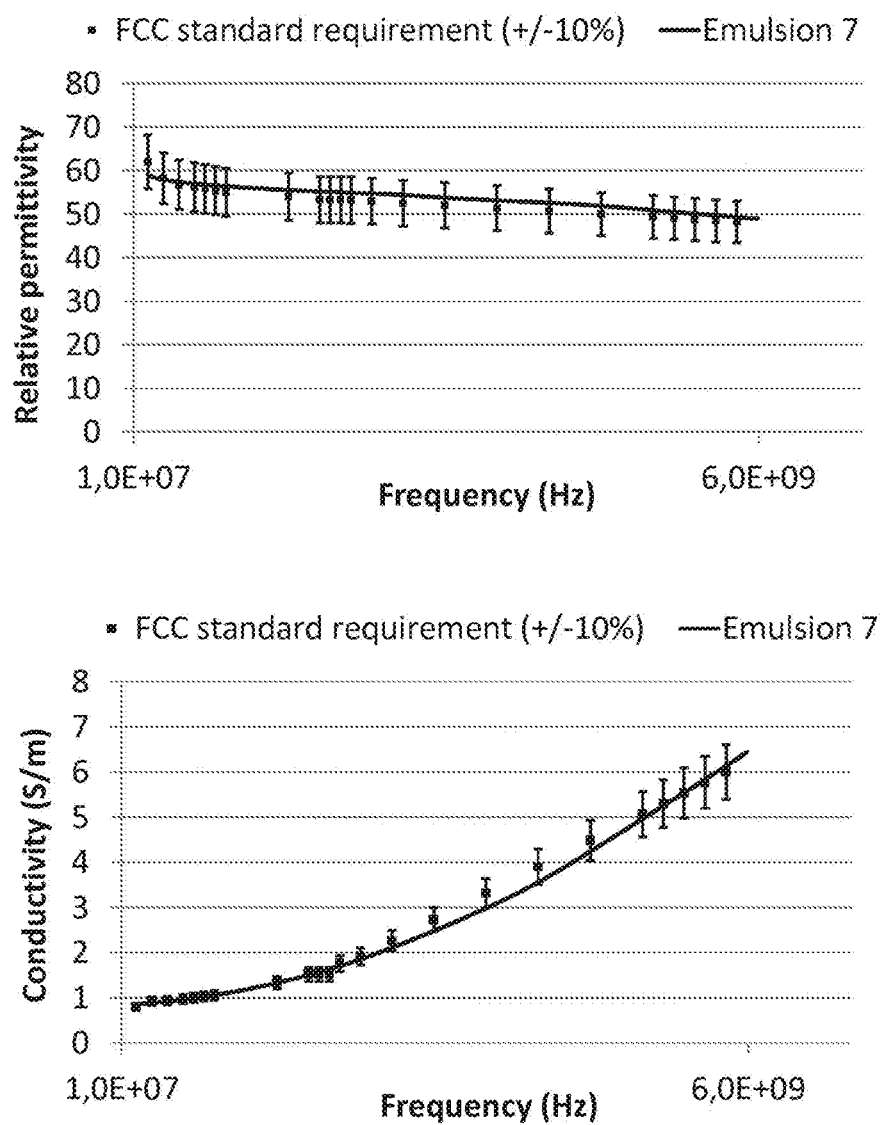
FIG. 7 represents the dielectric properties of emulsion 7 of example 6 compared to FCC regulatory requirements with +/−10% deviations, from 0.15 GHz to 6 GHz.

Dielectric Properties:

The dielectric properties of exemplified emulsion 7 were measured using the general method described above. Results presented in FIG. 7 (0.15 GHz to 6 GHz), show that the emulsion approaches FCC OET Bulletin 65 Supplement C target values within a +/−10% tolerance.

The invention claimed is:

1. Oil-in-water emulsion, comprising:
   water,
   from 15% to 35% in weight relative to the total weight of the aqueous phase of glycerol,
   from 0.6% to 1.2% in weight relative to the total weight of the emulsion of CaCl$_2$;
   optionally from 0.3% to 2% in weight of the total weight of the emulsion of xanthan,
   from 15% to 25% in weight relative to the total weight of the emulsion of isopropyl palmitate, and
   from 6 to 8% in weight relative to the total weight of the emulsion of a mixture of (i) surfactant having polyethylene oxide and chains and at least one aromatic group and (ii) sorbitan esters and/or ethoxylated sorbitan ester.

2. Oil-in-water emulsion according to claim 1, having a viscosity ranging from 0.005 Pa·s to 50 Pa·s at 25° C.

3. Oil-in-water emulsion according to claim 1, having a relative permittivity ranging from 68.09 to 31.2 and a conductivity ranging from 0.68 S/m to 6.60 S/m for frequencies ranging from 30 MHz to 6 GHz.

4. Device comprising:
   the emulsion according to claim 1,
   a simulated human body part filled with said emulsion; and
   at least one system capable of measuring a local specific absorption rate when the simulated human body part is exposed to an electromagnetic field.

5. Device according to claim 4, wherein the simulated human body part is a container in the form of part or all of a human head or part or all of a human trunk.

6. Method for conducting specific absorption rate tests of an apparatus radiating an electromagnetic field comprising:
   positioning the apparatus on or near the device according to claim 4; and
   measuring a field strength within the device when the apparatus under test is transmitting.

7. Oil-in-water emulsion, comprising:
   water,
   from 2% to 7% in weight relative to the total weight of the aqueous phase of glycerol,
   from 0.1% to 1% in weight relative to the total weight of the emulsion of CaCl$_2$;
   optionally from 0.3% to 2% in weight of the total weight of the emulsion of xanthan,
   from 10% to 15% in weight relative to the total weight of the emulsion of isopropyl palmitate, and
   from 6 to 8% in weight relative to the total weight of the emulsion of a mixture of (i) surfactant having polyethylene oxide and chains and at least one aromatic group and (ii) sorbitan esters and/or ethoxylated sorbitan ester.

8. Oil-in-water emulsion according to claim 7, having a viscosity ranging from 0.005 Pa·s to 50 Pa·s at 25° C.

9. Oil-in-water emulsion according to claim 7, having a relative permittivity ranging from 68.09 to 31.2 and a conductivity ranging from 0.68 S/m to 6.60 S/m for frequencies ranging from 30 MHz to 6 GHz.

10. Device comprising:
    the emulsion according to claim 7,
    a simulated human body part filled with said emulsion; and
    at least one system capable of measuring a local specific absorption rate when the simulated human body part is exposed to an electromagnetic field.

11. Device according to claim 10, wherein the simulated human body part is a container in the form of part or all of a human head or part or all of a human trunk.

12. Method for conducting specific absorption rate tests of an apparatus radiating an electromagnetic field comprising:
    positioning the apparatus on or near the device according to claim 10; and
    measuring a field strength within the device when the apparatus under test is transmitting.

\* \* \* \* \*